(12) United States Patent
Barbosa

(10) Patent No.: US 10,725,031 B1
(45) Date of Patent: Jul. 28, 2020

(54) REFLUX DEVICE FOR DETECTION OF ANALYTES IN SAMPLES

(71) Applicant: Maria D. F. S. Barbosa, Philadelphia, PA (US)

(72) Inventor: Maria D. F. S. Barbosa, Philadelphia, PA (US)

(73) Assignee: ConquerAb Inc., Tucson, AZ (US)

( * ) Notice: Subject to any disclaimer, the term of this patent is extended or adjusted under 35 U.S.C. 154(b) by 306 days.

(21) Appl. No.: 15/933,083

(22) Filed: Mar. 22, 2018

Related U.S. Application Data

(60) Provisional application No. 62/490,051, filed on Apr. 26, 2017.

(51) Int. Cl.
  *G01N 33/00* (2006.01)
  *G01N 33/543* (2006.01)
  *B01L 3/00* (2006.01)

(52) U.S. Cl.
  CPC ...... *G01N 33/54386* (2013.01); *B01L 3/5023* (2013.01); *G01N 33/54393* (2013.01); *B01L 2200/0647* (2013.01); *B01L 2200/10* (2013.01); *B01L 2300/047* (2013.01); *B01L 2300/069* (2013.01); *B01L 2300/0681* (2013.01); *B01L 2300/0825* (2013.01); *B01L 2300/0867* (2013.01)

(58) Field of Classification Search
  CPC .................. G01N 33/54386; G01N 33/54393
  See application file for complete search history.

(56) References Cited

U.S. PATENT DOCUMENTS

| | | | |
|---|---|---|---|
| 4,594,327 | A | 6/1986 | Zuk |
| 4,624,929 | A | 11/1986 | Ullman |
| 4,956,302 | A | 9/1990 | Gordon et al. |
| 5,186,843 | A | 2/1993 | Baumgardner et al. |
| 5,240,862 | A | 8/1993 | Koenhen et al. |
| 5,753,497 | A | 5/1998 | Bernstein et al. |
| 5,939,331 | A | 8/1999 | Burd et al. |
| 6,528,321 | B1 | 3/2003 | Fitzgerald et al. |
| 6,673,628 | B2 | 1/2004 | Freitag et al. |
| 8,535,617 | B2 | 9/2013 | MacDonald et al. |
| 9,903,866 | B2 | 2/2018 | Barbosa |

(Continued)

OTHER PUBLICATIONS

Article titled "Rapid, Sensitive, and Specific Lateral-Flow Immunochromatographic Point-of-Care Device for Detection of Herpes Simplex Virus Type 2-Specific Immunoglobulin G Antibodies in Serum and Whole Blood" by Laderman et al. and published in Jan. 2008 (Year: 2008).*

(Continued)

*Primary Examiner* — Blake A Tankersley

(57) ABSTRACT

Devices for detection of analytes in samples of various complexities are provided. The devices allow reflux of liquid into a sample-receiving member, providing for suitable analyte dilution and preventing leakage of cells or particulate material into the signal generation member. In one aspect, the devices are used to test analytes in biological samples such as blood, serum, plasma or other body fluids. In another aspect, the devices are used to test samples from tissues, such as organ tissues, tumor samples, or other body parts. In a further aspect, the devices are used to test microbial samples, food samples, or any other sample from which the analyte of interest can be captured into the reflux device.

14 Claims, 4 Drawing Sheets

(56) References Cited

U.S. PATENT DOCUMENTS

| | | | | |
|---|---|---|---|---|
| 2002/0173050 | A1* | 11/2002 | DiNello | B01L 3/5023 436/518 |
| 2006/0051237 | A1* | 3/2006 | Wang | B01L 3/5023 422/417 |
| 2010/0075352 | A1* | 3/2010 | Umegae | G01N 33/525 435/14 |
| 2013/0217136 | A1* | 8/2013 | Nazareth | G01N 33/54386 436/86 |

OTHER PUBLICATIONS

Laderman, E. I. et al. Rapid, Sensitive, and Specific Lateral-Flow Immunochromatographic Point-of-Care Device . . . Clinical and Vaccine Immunology 2008 p. 159-163, vol. 15, No. 1.

* cited by examiner

REFLUX DEVICE FOR DETECTION OF ANALYTES IN SAMPLES

CLAIM OF PRIORITY

This application claims priority to U.S. Provisional Patent Application No. 62/490,051 filed on Apr. 26, 2017, which is hereby incorporated by reference in its entirety.

FIELD OF INVENTION

Devices for detection of analytes in samples, including but not limited to complex biological specimens such as blood and tissues.

BACKGROUND OF THE INVENTION

Devices to test biological samples may have a sample-receiving zone that is distinct from the testing zone. As a non-limiting example, devices employing lateral flow technology have a sample-receiving zone, and the analytes flow towards the reaction zone. To retain red blood cells and/or other sample components that may interfere with the assay, a filter may be placed at or near the sample-receiving zone. However, cells or particulate materials escaping the filter can move through the device, causing high background and/or assay interference. Those limitations are more pronounced when the sample volume is variable, for example when the sample is blood obtained by pricking a finger, or when the amount of particulates in the sample is not exactly known. The sample size variability adds a need to pipette blood samples for volume consistency (Laderman, E. I. et al. 2008 Clinical and Vaccine Immunology 15: 159-163; expressly incorporated by reference herein), which is both unpractical and can result in errors during routine point of care and/or patient self-testing.

Volumes ranging from less than 1 µl to more than 20 µl can result from a finger pricking, depending on factors such as the finger (Thumb, index, middle, ring or baby finger), gender (male or female), size of the hand, blood vessels at the specific area where the lancet is introduced, and pressure applied to the finger. Those sources of variability can render use of filters to separate red blood cells ineffective: filter of one given size and thickness may be too small to retain all blood cells from a large blood drop, resulting in leakage; conversely, if the filter is made too large, it may retain samples, preventing them form reaching a test zone. The use of a pre-determined volume of blood requires blood collection, followed by pipetting of the desired volume. Besides, in some cases multiple finger pricking may be required to collect the required blood volume. Variability is also intrinsic to other complex samples; dilution with a liquid may be necessary to make the analyte available for testing. As a non-limiting example, grounded biological tissues can display uneven characteristics in terms of amount of particulates versus other components.

An effective point of care device for testing blood samples should be simple to operate, allowing either patients or health care providers to consistently execute the test by pricking a finger once, without requiring, for example, multiple finger pricking to separate plasma prior to the test. There is also an unmet need for said devices and rapid diagnostics for testing a wide variety of complex samples, containing solid or particulate matter. In addition, the device should also be effective when used with less complex samples, for example plasma or other fluids.

To avoid hook effect and/or to allow optimal flow of analytes from the sample, and/or to minimize matrix assay interference, a dilution of the sample is often times required in assays. "Hook effect", as defined herein, is meant assay interference caused by very high concentrations of analyte. Another limitation with currently available device formats is that they do not allow for consistent flow of buffers, and hence introduce the need for pipetting in order to add measured buffers to the device. That is not practical for one unskilled in the art to perform, and also can add additional variability due to factors such as pipetting mistakes, buffer preparation, and calibration.

Although filters and complex materials such as ones used for separating erythrocytes from whole blood are known in the art [U.S. Pat. No. 5,186,843; expressly incorporated by reference herein], they do not solve the above-described limitations.

In addition, when liquid is applied directly over the sample-receiving zone, an additional problem is created, in that the liquid flow further favors movement of cells and/or other particulates towards the testing zone.

Testing of biological samples such as tissues suffer from similar limitations as described above. It should be noted that in the case of blood and/or some other complex samples, the possibility of contamination with contagious agents might render unpractical a device that needs to be assembled during use.

There is an unmet need for a simple analyte-detecting device with the following characteristics: (i) can be used by ones not skilled in the art, for example patients, or point of care providers; (ii) the parts are contained within the device, no need to pipette liquids; (iii) is operable within a range of sample volumes, thereby being suitable for samples such as one small blood drop (less than 5 µl), while still providing acceptable results with larger sample volumes.

BRIEF SUMMARY OF THE INVENTION

This invention is directed to devices for detection of analytes in samples of various complexities and sizes. The parts are assembled, resulting in self-contained devices, which facilitates testing by users not skilled in the art. The device allows for reflux of liquid into the sample receiving member, providing suitable analyte dilution and preventing leakage of particulate material into the signal generation member. In one aspect, the device is used to test analytes in biological samples such as blood, serum, plasma or other body fluids. In another aspect, the device is used to test samples from tissues, such as organ tissues, tumor samples, or other body parts. In a further aspect, the device is used to test microbial samples, food samples, or any other sample from which the analyte of interest can be captured into the reflux device. The analyte captured at the reaction zone can be a nucleic acid, including oligonucleotides, or amino acid, or protein, or peptide, or lipid, or carbohydrate, or chemical compound or entity, or any combination of those, or any entity that can react and generate a signal. The analyte can be organic or inorganic, naturally occurring or engineered, synthesized or a combination of those. In another aspect, the analyte can be of a nucleic acid, or protein, or lipidic, or carbohydrate nature, or chemical nature, or a chemical compound or entity, or a combination of those.

Samples flow from A to B. 1, no anti-adalimumab antibody in the buffer sample; 2, anti-adalimumab antibody (HCA204; AbD Serotec) spiked on the buffer sample; 3, anti-adalimumab antibody spiked in blood (HCA204; AbD Serotec). Following sample application, 80 µl of buffer was added to the edge of the sample pad (position A), upstream from the sample. "Chimeric-adalimumab" is antibody anti-hTNF-α-mIgG2a (InvivoGen) immobilized on the membrane; "Control" is rabbit antibody anti-goat IgG Fc (Thermo Fisher Scientific).

Figure 7:
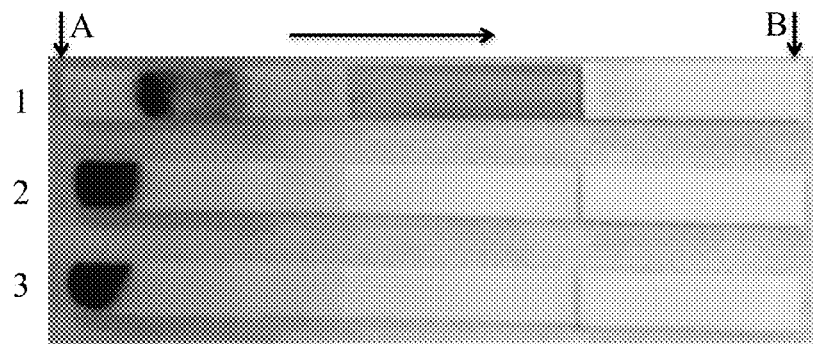

FIG. 7. Test strips for lateral flow assay, composed of (in this order): a sample pad; a second pad; a membrane; an absorbent pad. Samples are applied at position A and flow toward position B. 1, 100 µl 0.9% NaCl dispensed at position A, upstream from a blood sample; 2, 100 µl of buffer (10 mM phosphate buffer pH 7.4, plus 137 mM NaCl, plus 0.02% triton-X-100) was dispensed downstream from a blood sample in a 45° angle, and in a direction opposite to the direction of sample flow, creating a reflux; 3, 100 µl of 0.9% NaCl was dispensed downstream from a blood sample in a 45° angle, and in a direction opposite to the direction of sample flow, creating a reflux.

Figure 8:
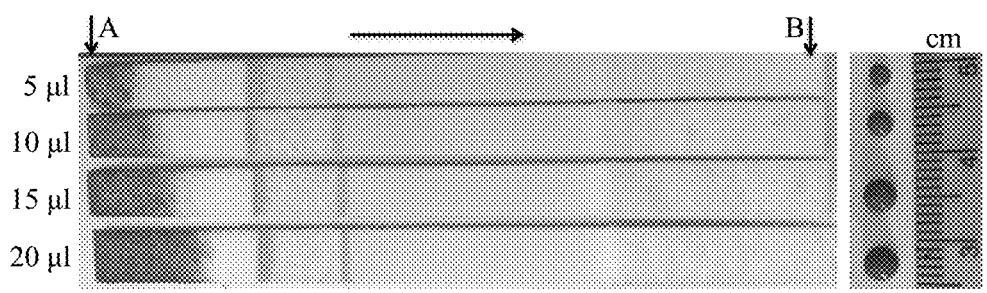

FIG. 8. Test strips for lateral flow assay, composed of (in this order): a sample receiving pad; a second pad; a membrane; an absorbent pad. Samples flow from A to B. Different blood volumes were applied to the sample pad, followed by buffer (10 mM phosphate buffer pH 7.4, plus 137 mM NaCl, plus 0.02% triton-X-100) applied in an angle downstream from the sample, and in a direction opposite to the direction of sample flow, creating a reflux. Equivalent blood drops are shown to the right.

Figure 9:
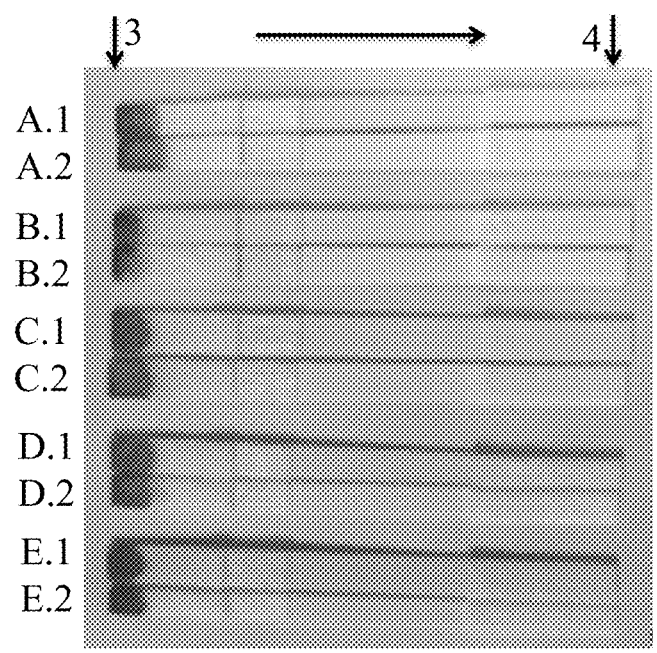

FIG. 9. Test strips for lateral flow assay, composed of (in this order): a sample pad; a second pad; a membrane; an absorbent pad. Samples flow from position 3 to position 4. 5 µl of blood was applied to each sample pad, followed by buffer (10 mM phosphate buffer pH 7.4, plus 137 mM NaCl, plus 0.02% triton-X-100) applied in an angle downstream from the sample, and in a direction contrary to the sample flow, to create a reflux. 50 µl of buffer was applied to A1, B1, C1, D1, and E1. 100 µl of buffer was applied to A2, B2, C2, D2, and E2. The composition of the sample pads was as follows: A, LF1 (Whatman); B, VF2 (Whatman); C, CytoSep 1660 (Ahlstrom); D, CytoSep 1662 (Ahlstrom); E, CytoSep HV grade 1667 (Ahlstrom).

Figure 10:
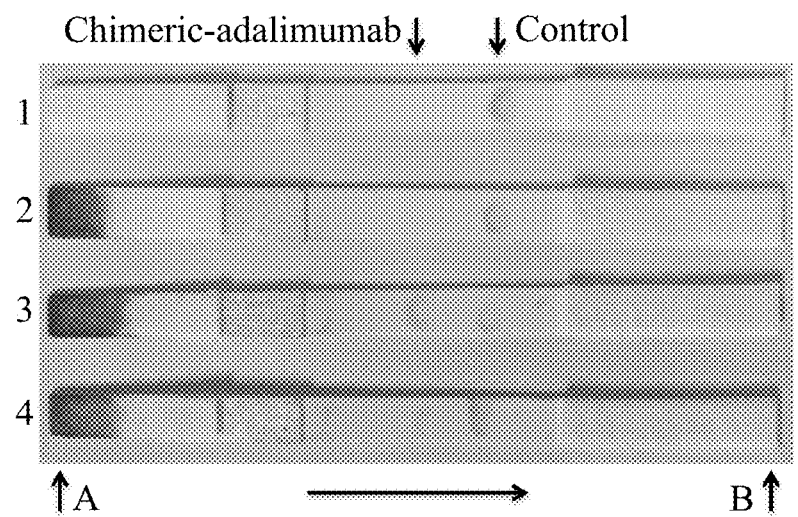

FIG. 10. Test strips for lateral flow immunoassay of anti-adalimumab antibodies composed of (in this order): a sample pad; a second pad; a membrane; an absorbent pad. Samples flow from position A to position B. 1, buffer only; 2, blood sample; 3 and 4, anti-adalimumab antibody (HCA204; AbD Serotec) spiked in 5 µl of blood samples. Following sample application, 50 µl of buffer was added downstream from the sample in an angle, and in a direction contrary to the sample flow, generating a reflux. "Chimeric-adalimumab" is antibody anti-hTNF-α-mIgG2a (InvivoGen) immobilized on the membrane; "Control" is rabbit antibody anti-goat IgG Fc (Thermo Fisher Scientific).

Figure 11:
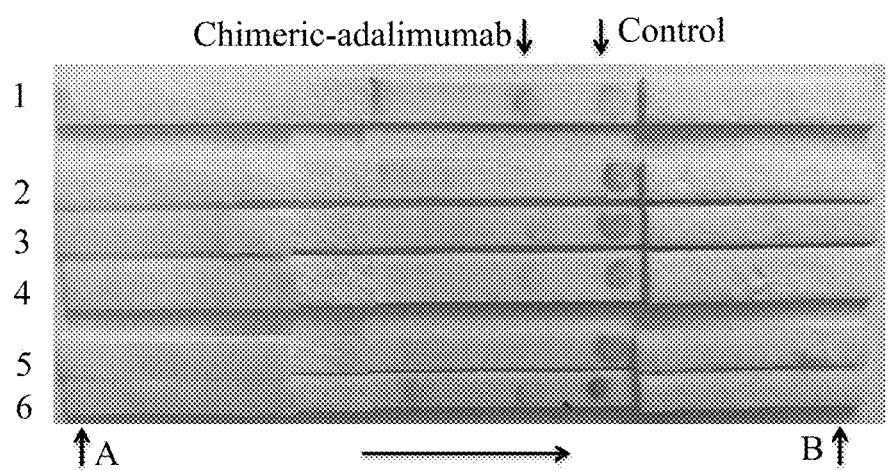

FIG. 11. Test strips for lateral flow assay, composed of (in this order): a sample pad (VF2; Whatman); a pad containing latex-labeled anti-human IgG; a membrane where both a control antibody and a chimeric antibody were immobilized, the latter being composed of the adalimumab variable region fused with mouse IgG2a constant region; an absorbent pad. "Chimeric-adalimumab" is antibody anti-hTNF-α-mIgG2a (InvivoGen) immobilized on the membrane; "Control" is rabbit antibody anti-goat IgG Fc (Thermo Fisher Scientific). 1, anti-adalimumab antibody (HCA204; AbD Serotec) in buffer; 2, buffer with 10% human plasma; 3 and 4, anti-adalimumab antibody (HCA204; AbD Serotec) in buffer with 10% human plasma; 5, buffer with 10% human serum; 6, anti-adalimumab antibody (HCA204; AbD Serotec) in buffer containing 10% human serum. The samples flow from A to B.

DETAILED DESCRIPTION OF THE INVENTION

Devices to detect analytes in samples of various complexities are included in embodiments of the present invention. In order that the invention may be more completely understood, several definitions are set forth below. Such definitions are meant to encompass grammatical equivalents.

A "device" as used herein is meant to comprise diagnostics and apparatus.

By 'ADA" as used herein is meant an anti-drug antibody that bind to a protein or other entity or target antigen, whereas that protein or other entity or antigen can be a therapeutic agent or other. In that sense, all antibodies are essentially "binding".

By "anti-drug antibody" as used herein is meant an antibody generated as an immune response to an entity, said entity including but not restricted to therapeutic proteins. A therapeutic drug may be, without limitations, a carbohydrate, or protein, or peptide, or lipid, or nucleic acid, or oligonucleotide, or chemical entity or other entities, or combinations of the above.

By "adverse event" as used herein is meant any undesirable experience (i.e., a bad side effect) associated with the use of a product.

By "antibody" as used herein is meant a protein that binds an amino acid sequence or another entity. In mammals such as humans and mice, antibodies contain paired heavy and light polypeptide chains. Each chain contains a variable and a constant region. The variable regions of the light and heavy chains are required for binding the target antigen.

By "labeled entities" as defined herein are entities that can bind to the constant region of an antibody and/or to other molecules. A variety of labels can be used. Said entities can be selected from the group consisting of protein, or peptide, or lipid, or oligonucleotide, or carbohydrate, or chemical entity, or any entity that can have a suitable label.

By "low binding propensity" as described herein is meant a decreased affinity for binding, when compared with conditions and entities in which said affinity would be high. Of note, said propensity is not defined in absolute terms. For example, a monoclonal antibody specifically directed to the constant region ("Fc") of an IgG1 therapeutic human antibody may have a low binding affinity ("$K_D$") for said Fc region; however, said antibody may have high binding propensity for that human Fc by comparison with the binding to a mouse IgG2a constant region. The amino acid identity between said constant regions of mouse and human is often less than 50%. This non-limiting example is given for better understanding, without constraining the definition to exclude other entities or combinations thereof.

By "$K_D$" as defined herein is meant a dissociation constant, which is a specific type of equilibrium constant, and is sometimes used to provide a quantitative measurement of antibody affinity.

By "chimeric protein" as used herein is meant a protein or a segment of a protein, wherein said protein or segment contains one or more target antigens and is fused with an entity, wherein said entity is from the group consisting of protein, peptide, lipid, carbohydrate, oligonucleotide, chemical entity or moiety, or a combination of any of the above. As a non-limiting example, a variable region of a human IgG1 antibody drug fused with the constant region of a mouse IgG2a antibody or with a chemical entity is a chimeric protein as defined herein.

By "antibody epitope" as used herein is meant the region of the target antigen that binds to the antibody variable region.

By "antigen" as used herein is meant a substance that induces an immune response. By "target antigen", as used herein is meant the antigen that is bound specifically by the variable region of a given antibody. A target antigen may be, without limitations, a peptide, a protein, a region of a protein, carbohydrate, lipid, nucleic acid, oligonucleotide, chemical entity, haptens, or any combination of the above.

By "amino acid" as used herein is meant one of the 20 naturally occurring amino acids or any non-natural analogues.

By "app" is meant an "application", which includes a specialized program that can be used with a mobile device or a computer.

By "assay" as used herein is meant a procedure for testing samples. By "pad" as used herein is meant a material capable of absorbing liquid; said liquid may flow from the pad in one or more directions. A pad can be paper, or cellulose fibers, or a cotton material, or mixed cellulose ester, or synthetic fibers, or other materials, or a combination of materials.

By "biobetter" as used herein is meant a newer version of a marketed biotherapeutic.

By "biosimilar' as used herein is meant a therapeutic protein (biotherapeutic) similar to another one already marketed for which the patent has expired (the "reference product").

By "big data" is meant large volume of patient records derived from physician-supervised treatment and/or insurance company claims. Sometimes referred to as "megadata".

By "biotherapeutic" as used herein is meant a therapeutic entity that comprises a protein or peptide (biologic drug).

By "chemistry, manufacturing and control (CMC)" factors as used herein is meant product quality factors such as impurities, contaminants, aggregates and other product-related degradants, factors resulting from the recombinant expression system used for proteins (such as nonhuman glycosylation), factors resulting of the protein design (for example, change in aggregation pattern as a result of PEGylation).

By "database" as used herein is meant a structured combination of information and/or data analyses.

By "distributed analysis" as used herein is meant "an analysis that is distributed across multiple computers simultaneously; following the parallel computations, the results are combined centrally" (Barbosa, M. D. F. S. and Smith, D. D. 2014 Drug Discov. Today 19: 1897-1912; expressly incorporated by reference herein).

By "fluorescent label" is meant any molecule that may be detected based on its fluorescent properties. Suitable fluorescent labels include, but are not limited to fluorescein, rhodamine, tetramethylrhodamine, eosin, erythrosin, malacite green, stilbene, Lucifer Yellow, Cascade Blue®, Cascade Yellow, Texas Red®, IAEDANS, EDANS, BODIPY® FL, LC Red 640, Cy®5, Cyanine5.5, LC Red 705, Oregon Green® 488, Alexa-Fluor® dyes, R-phycoerythrin, fluorescein isothiocyanate (FITC), Texas Red®. Other appropriate optical dyes can also be used.

By "full length antibody" as used herein is meant the structure that constitutes the natural biological form of an antibody, including variable and constant regions, including one or more modifications. Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each. In certain variations, antibody may mean a protein consisting of one or more polypeptides substantially encoded by all or part of the recognized immunoglobulin genes. Antibody herein is meant to include full-length antibodies and antibody fragments, and may refer to a natural antibody from any organism, an engineered antibody, or an antibody generated by recombinant techniques for experimental, therapeutic, or other purposes.

By "IgG" as used herein is meant a polypeptide belonging to the class of antibodies that are substantially encoded by a recognized immunoglobulin gamma gene. In humans this class comprises IgG1, IgG2, IgG3, and IgG4. Also included are hybrids of IgG proteins in which amino acids for one IgG protein substituted for amino acids of a different IgG protein (e.g. IgG1/IgG2 hybrids).

By "immunogenicity" as used herein is meant the ability of a protein or another substance or entity to elicit a host's immune response.

By "immunoglobulin (Ig)" herein is meant a protein consisting of one or more polypeptides substantially encoded by immunoglobulin genes. Immunoglobulins may have a number of structural forms, including but not limited to full-length antibodies, antibody fragments, and individual immunoglobulin domains. Immunoglobulins include but are not limited to antibodies.

By "isotype" as used herein in regards to antibodies, is meant any of the subclasses of immunoglobulins defined by the chemical and antigenic characteristics of their constant regions. The currently known human immunoglobulin isotypes are IgG1, IgG2, IgG3, IgG4, IgA1, IgA2, IgM1, IgM2, IgD, and IgE.

By "labeled Antibodies" as used herein is meant antibodies that have the addition of one or more labels. Gold-labeled anti-host antibodies are a non-limiting example of labeled antibodies that can be used to detect antigen-antibody complexes.

The term "labeling group" or "label" as used herein in conjunction with the term "labeled" means any detectable label. In some embodiments, the labeling group is coupled to the antibody via spacer arms of various lengths to reduce potential steric hindrance. Various methods for labeling proteins are known in the art and may be used in performing the present invention. In general, currently known labels fall into a variety of classes, depending on the assay in which they are to be detected. For example: a) isotopic labels, which may be radioactive; b) magnetic labels; c) redox active moieties; d) optical dyes; e) enzymatic groups such as horseradish peroxidase, beta.-galactosidase, luciferase, alkaline phosphatase; f) biotinylated groups. Various methods for labeling proteins or other entities are known in the art and may be used in performing the present invention. Specific labels can include but are not limited to optical dyes, including, but not limited to, chromophores, phosphors and fluorophores. Fluorophores can be either "small molecule" (chemical entity) or protein, or a combination.

By "lateral flow" or "lateral flow technology" or "lateral flow assay" as used herein is meant a technology or assay based on the principle that the test substance and/or reagents flow in one (or more than one) direction, and may result in detection of a test substance (Ahn, J. S. et al. 2003 Clin. Chim. Acta 332:51-59; Chan, C. P. et al. 2003 J. Immunol. Methods 279: 91-100; Choi, D. H. et al. 2010 Biosens. Bioelectron. 25: 1999-2002; Chowdry, V. K. 2014 J. Virol. Methods 197: 14-18; Choi, S. et al. 2004 Clin. Chim. Acta 339: 147-156; Corstjens, P. 2011 Clin. Biochem. 44: 1241-1246; Corstjens, P. L. et al. 2016 Clin. Biochem. 49: 22-31; Geertruida, A. et al. 2009 Anal. Bioanal. Chem. 393: 569-582; Koizumi, D. et al. 2014 Food Chem. 150: 348-352; Laderman, E. I. et al. 2008 Clin. Vaccine Immunol. 15: 159-163; Linares, E. M. et al. 2012. J. Immunol. Methods 375:264-270; Lu, S. Y. 2012 Anal. Biochem. 422: 59-65; Nabatiyan, A. et al. 2010 J. Acquir. Immune Defic. Syndr. 53: 55-61; Nielsen, K. 2008 J. Immunoassay Immunochem. 29: 10-18; Nielsen, K. et al. 2009 J. Immunoassay Immunochem. 30: 313-321; Oem, J. K. 2009 Clin. Vaccine immunol. 16: 1660-1664; Offermann, N. 2014 J. Immunol. Methods 403: 1-6; Oh, Y. K. 2014 Biosens. Bioelectron. 61: 285-289; Peng, T. 2014 J. Food Prot. 10: 1824-1829; Rundstrom, G. 2007 Clin. Chem. 53: 342-348; Song, X. and Knotts, M. 2008 Anal. Chim. Acta 626: 186-192; Teerinen, T. 2014 Anal. Bioanal. Chem. 406: 5955-5965; van Dam. G. J. et al. 2013 Exp. Parasitol. 135: 274-282; Wilkinson, R. et al. 2003 Ann. N Y Acad. Sci. 990: 386-390; Yonekita, T. et al. 2013 J. Microbiol. Methods 93: 251-256; all expressly incorporated by reference herein). In another embodiment, vertical flow can be used.

By "NAb" or "neutralizing antibody" as used herein is generally meant antibody that "inhibits or reduces the pharmacological activity of the biologic drug molecule, as determined by an in vitro test or animal-based bioassay method, regardless of its in vivo clinical relevance (i.e., whether or not test method results relate to clinical impact in the subject)". Furthermore, within the general scope of this definition, the term "NAb" can be used for an antibody directed against any other entity or target antigen.

By "PEGylation" as used herein is meant the addition of one or more polyethylene glycol (PEG) moiety by various means that may comprise the use of linkers.

A "patient" for the purposes of the present invention includes both human and other animals, preferably mammals and most preferably humans.

By "pharmacoepidemiology" as used herein is meant the use of population-based studies to monitor drug safety.

By "pharmacovigilance" as used herein is meant scientific and data gathering activities relating to the detection, assessment and understanding of adverse events associated with pharmaceutical products.

By "postmarketing" as used herein is meant after a therapeutic drug has received approval from a regulatory agency, for example the U.S. Food and Drug Administration (FDA) or the European Medicines Agency (EMA).

By "pre-existing antibody" as used herein, is meant an antibody against an antigen that was present in the body of a human or animal prior to exposure to said antigen.

By "protein" herein is meant attached amino acids. The protein may be made up of naturally occurring amino acids and peptide bonds, or synthetic peptidomimetic structures, i.e. "analogs", such as peptoids (Simon, R. J. et al. 1992 Proc. Natl. Acad. Sci. USA 89: 9367-9371; expressly incorporated by reference herein). Thus "amino acid", or "peptide residue", as used herein encompasses both naturally occurring and synthetic amino acids.

By "target antigen" as used herein is meant the antigen that is bound specifically by the variable region of a given antibody. A target antigen may be a protein, or a region of a protein, or a peptide, or a carbohydrate, or a lipid, or a nucleic acid, or a oligonucleotide, or other entity, or a chemical compound, or a combination of two or more of the above.

By "tolerance" as used herein is meant immune tolerance to a protein or another substance or entity, typically characterized by the lack of immune responses.

The term "treatment" in the present invention is meant to include therapeutic treatment, as well as prophylactic, or suppressive measures for a disease or disorder. "Treatment" also encompasses administration of a therapeutic drug after the appearance of the disease in order to ameliorate, control, or to eradicate the disease. Those "in need of treatment" include mammals already having the disease or disorder, as well as those prone to having the disease or disorder, including those in which the disease or disorder is to be prevented.

By "variant protein", "protein variant", "variant polypeptide", or "polypeptide variant" as used herein is meant a polypeptide sequence that differs from that of a parent polypeptide sequence by virtue of at least one amino acid modification. Variant polypeptide may refer to the polypeptide itself, a composition comprising the polypeptide, or the amino sequence encoding it.

By "vertical flow" or "vertical flow technology" as used herein is meant a technology or assay based on the principle that the test substance and/or reagent flows vertically.

In one embodiment a device is provided, which allows detection of analytes in complex samples. The device allows for liquid release after sample dispensing in a direction contrary to the sample flow, creating a reflux which prevents cells, particulate materials or other solid components from entering the detection zone, while also providing suitable dilution of the analyte.

In a preferred embodiment, the device has two opposing liquid reservoirs. The first reservoir dispenses liquid towards the sample application site, creating a liquid reflux. The second reservoir subsequently dispenses liquid in the direction of sample flow, providing for washing of the any connecting material and of the detection zone.

In another preferred embodiment, the device has only one liquid reservoir that dispenses liquid in an angle towards the sample application site, creating a reflux.

In one embodiment, the device uses lateral flow technology and has different materials overlapping and sequentially ordered as follows: a sample pad; a pad containing labeled entities that bind to the analytes in the sample; a membrane containing immobilized entities on a detection zone, said entities being capable of binding to the labeled analyte, generating a signal. The signal can be colorimetric or other.

In another embodiment, the device of the present invention can detect analytes by generating a signal other than colorimetric, for example electrochemiluminescence, or when an electrical property is altered upon binding of ADA (U.S. Pat. No. 4,219,335; expressly incorporated by reference herein). Said electrical property includes one or more of the following: resistance; impedance; capacitance; electrical potential. Other methods to detect a signal upon binding of sample ADAs can be employed, and are included within embodiments of the present invention. Carbon nanotube biosensors are also included within embodiments of the present invention (U.S. Pat. No. 8,716,029 B1). Also included in embodiments of the present invention are other techniques that can be connected to the reflux principle described herein; paper microfluidics is a non-limiting example (Asano, H. and Shiraishi, Y. 2015 Analytica Chimica Acta 883: 55-60; expressly incorporated by reference herein).

Measurement of Alanine Aminotransferase . . . PLoS One 2015, e01281111, vol. 10, No. 5

In another embodiment, lateral flow or vertical flow can be used. In another embodiment, the reactions of the device and/or diagnostic can be performed with limited flow of reagents or samples.

In another embodiment, proteins and/or other molecules can be labeled and used for generation of assay signal. In some embodiments, labels can be used in various forms to generate a detectable signal. The assay readout can be either the signal generated or inhibition of signal.

Appropriate proteinaceous labels also include, but are not limited to, green fluorescent protein (GFP) including from *Renilla, Ptilosarcus*, or *Aequorea* species, blue fluorescent protein, yellow fluorescent protein, luciferase, and beta galactosidase.

Colloidal-gold, silver enhanced gold, latex bead and carbon black nanoparticles are labels known in the art that can also be utilized for the present invention. Other labels capable of generating a suitable signal can also be used.

In another embodiment, novel labels discovered by any techniques, including but not restricted to genetic analysis of different species, or by any chemical, biochemical or other means, can be incorporated in assays used in embodiments of the present invention, and are within its scope.

The analyte detection with the device and/or diagnostic can be qualitative or quantitative. Qualitative results can be observed (but are not restricted to) by visual inspection or other means of capturing a signal.

In another embodiment, the device is associated with an app.

In another embodiment, the device can be used to test antibodies against therapeutic drugs (Barbosa, M. D. F. S. and Smith, D. D. 2014. Drug Discov. Today 19: 1897-1912; U.S. Pat. No. 9,903,866; expressly incorporated by reference herein). In some embodiments the therapeutic drug is a bisimilar or a biobetter (Barbosa, M. D. F. S. and Smith, D. D. 2014 Drug Discov. Today 19: 1897-1912; expressly incorporated by reference herein).

Therapeutic drugs that have been tested in humans can be either natural products, or small molecule drugs, or peptides, or therapeutic proteins (biotherapeutics), or small-molecule-biotherapeutic conjugates, or oligonucleotide therapies (Barbosa, M. D. F. S. et al. 2013 Anal. Biochem. 441: 174-179; Barbosa, M. D. F. S. and Smith, D. D. 2014 Drug Discov. Today 19: 1897-1912; Woodcock, J. et al. 2007 Nat. Rev. Drug Discov. 6: 437-442; Lundin, K. et al. 2015 Human Gene Therapy 26: 475-485; all expressly incorporated by reference herein). Combination therapies (in which more than one entity is used) are also common. Complex therapeutic drugs and gene therapy are also included within the scope of therapeutic agents. In one preferred embodiment, the device is used to detect antibodies against therapeutic drugs. In another preferred embodiment, the reagent immobilized on the detection zone is a therapeutic drug, or a segment of a therapeutic drug, either alone or fused with other entity (U.S. Pat. No. 9,903,866; expressly incorporated by reference herein).

In another embodiment, the therapeutic drug is a vaccine, meaning the drug is administered to elicit a host immune response.

In an alternate embodiment, data obtained with the devices are used to generate databases and are used to associate genetic components with risk of adverse events or likelihood of drug efficacy. In another embodiment, the information organized within databases, used alone or in combination with additional individual testing, can be used to evaluate postmarketing drug efficacy and/or safety (Patent application US2016-0320405 A1; expressly incorporated by reference herein).

In another embodiment, the devices of the present invention contain information allowing access to databases. Said information can be, but is not restricted to, a code on the device, or on the device's package. Various levels of security and access can be applied to the databases. For example, a device that that tests for ADAs against insulin may also contain a code allowing access to a section of the database that contains data pertaining to evaluation of efficacy or safety of insulin products, without allowing access for example to a section of the database that contains data pertaining to interferon-β drugs. Those security levels and access can be changed if deemed appropriated. These examples are meant to illustrate the versatility of the devices, without constraining their use or construction.

Results obtained with devices in one embodiment of the present invention may be compared with one or more conventional assay. The parameters tested may include but are not limited to factors such as sensitivity, robustness, inter and intra assay variation, precision, sensitivity, matrix interference, cut point determination, minimal required dilution, and drug inhibition of the assay.

The devices of one embodiment of the present invention may be further validated in clinical and/or preclinical studies. That validation may include but not be restricted to comparison of data obtained with samples from the same humans or animal models. Other forms of device validation may also be used.

In another embodiment, the devices of the present invention are used to assess risk of immune reactions (Barbosa, M. D. F. S. and Smith, D. D. 2014 Drug Disc. Today. 12:1897-1912; expressly incorporated by reference herein).

In another embodiment, distributed analysis may be used when building, updating or consulting databases that incorporate data obtained with the device of the present invention.

Included in the present invention are diagnostic tests to identify patients who are likely to show a favorable clinical response to a therapeutic drug.

In another preferred embodiment, the device is used to compare immunogenicity of biotherapeutics.

In one embodiment, the device of the present invention may detect selected ADA isotypes. In another embodiment, the device of the present invention may comprise modifications to allow detection of all antibody isotypes. The testing devices may be tailored to detect individual samples or multiple samples. In another embodiment, the device and/or diagnostic may be used for antibody epitope mapping.

Non-limiting examples of modifications to increase sensitivity and accuracy of the device include optimization of the detection method and of sample collection and size, minimization of nonspecific background signal, optimization of materials used for device construction, optimization of reagent concentration immobilized on the device, selection of time for assay development and signal reading. In another embodiment, modifications are made to improve biophysical properties of the reagents used for the device construction, comprising one or more of the following: stability, solubility, and oligomeric state. Other improvements in device performance are also included within embodiments of the present invention.

The devices of the present invention can be used alone to provide information of the anti-drug antibody (ADA) positive or negative status of a patient or can be is used in conjunction with a database and with statistical analyses to infer the probability of safety or efficacy issues due to ADA responses. Those uses are included in embodiments of the present invention.

In another embodiment, the testing devices of the present invention can be used to guide selection of therapeutic drug dose.

In another preferred embodiment, the devices of the present invention can be used to determine immune status. That can be done, as a non-limiting example, by determining the presence of specific antibodies in patient blood. Testing immunization following vaccination and/or the need to receive a vaccine is included with embodiments of this invention. Non-limiting examples of vaccines included within some of the embodiments are vaccines for tetanus, diphtheria, hepatitis A, hepatitis B, yellow fever, measles, mumps, rubella, polio, varicella (chickenpox), and pertussis.

The device described herein can be used to assay the level of an analyte of interest, for example in a biological sample. Examples include, without limitations, toxins, organic compounds, polypeptides, microorganisms, bacteria, viruses, amino acids, peptides, proteins, nucleic acids, oligonucleotides, carbohydrates, lipids, hormones, steroids, vitamins, drugs (either therapeutic or ones administered for illicit purpose), pollutants, pesticides, and metabolites of or antibodies to any of the above substances. Any antigenic substance, hapten, antibody, macromolecule, and combinations thereof can also be an analyte assayed using the apparatus described herein.

In another preferred embodiment, the device can be used to test food contamination or patient exposure to an infectious agent.

In another preferred embodiment, the device of the present invention can be used to test anti-drug antibodies in humans or animals. Data collected may be used for statistical analyses to investigate correlations with genetics.

In another embodiment, the device of the present invention can be used to test analytes in patient samples during clinical trials and/or postmarketing.

In a preferred embodiment, the device is portable. In another preferred embodiment, the device is disposable. In a further preferred embodiment, the device can be hand-held or rest on a surface.

EXAMPLES

Example 1

Figure 1:
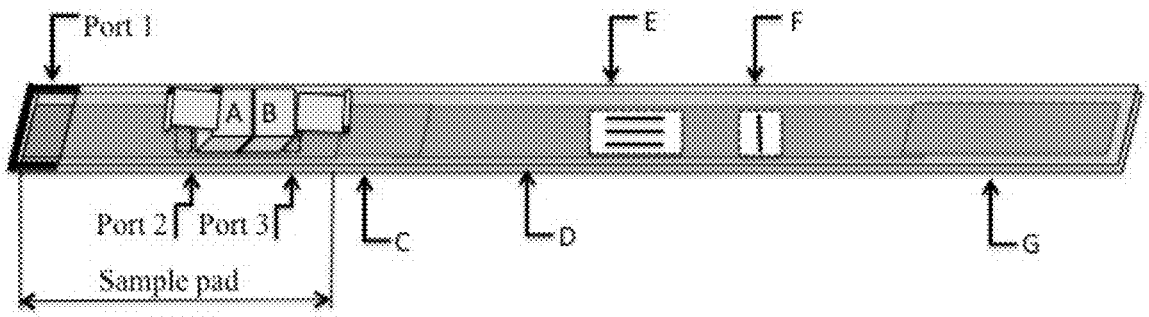
FIG. 1. Reflux device for detection of analytes in samples. Two pulling locking members (A and B) containing liquid, are positioned downstream from the sample-receiving Port 1. The sample flows from Port 1 to position G. Opening of the first locking member (Port 2) causes liquid to flow in the direction opposite to the sample flow, creating a reflux. Subsequent opening of the second locking member (Port 3) in the direction of sample flow washes the assembled components, which comprise a region where one or more immobilized reagents (E and F) can react with analytes in the sample, generating a signal.
Figure 2:
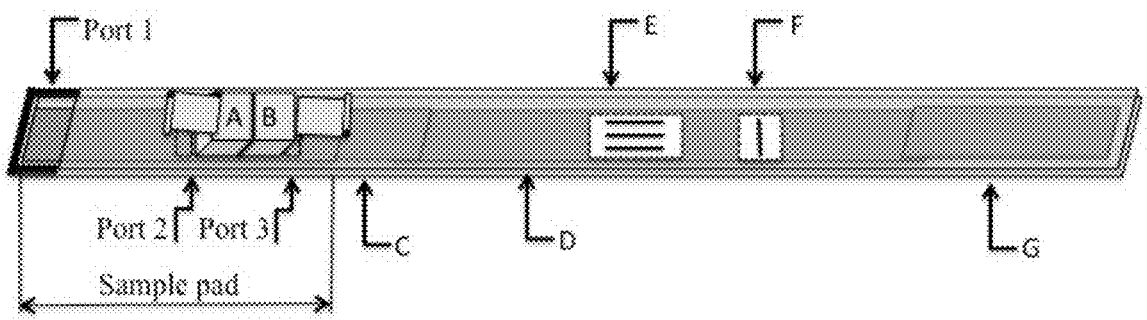
FIG. 2. Reflux device for detection of analytes in samples. Two sliding locking members (A and B) containing liquid, are positioned downstream from the sample-receiving Port 1. The sample flows from Port 1 to position G. Opening of the first locking member (Port 2) causes liquid to flow in the direction opposite to the sample flow, creating a reflux. Subsequent opening of the second locking member (Port 3) in the direction of sample flow washes the assembled components, which comprise a region where one or more immobilized reagents (E and F) can react with analytes in the sample, generating a signal.
Figure 3:
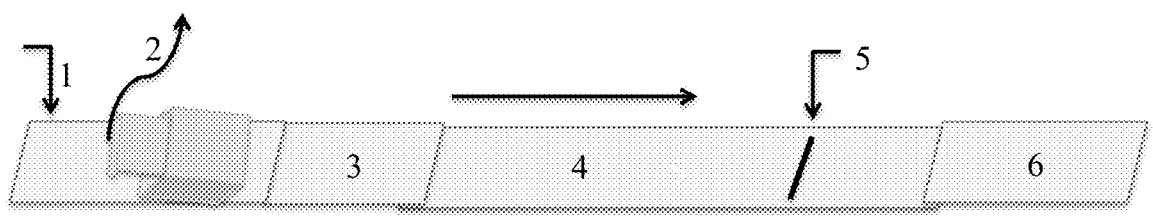
FIG. 3. Reflux device for detection of analytes in samples. One pulling or sliding locking member (2) is positioned downstream from the sample-receiving member (1). The sample flows from position 1 in the direction of position 6. The following components are sequentially positioned in the interior of the device: a sample-receiving pad (position 1), a second pad where labeled reagents are immobilized (position 3), a membrane (position 4) where capture reagents are immobilized (position 5), and another pad (position 6). Opening of the locking member causes liquid to flow in the direction opposite to the sample flow, creating a reflux. The liquid subsequently flows towards one or more immobilized reagents, which can react with analytes in the sample, generating a signal. A component is placed between the first component and the component containing immobilized reagents.
Figure 4:
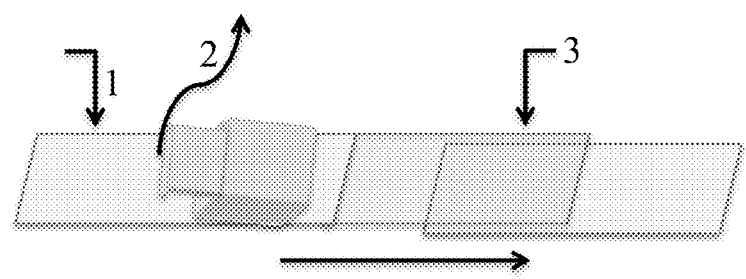
FIG. 4. Reflux device for detection of analytes in samples. One pulling or sliding locking member (2) is positioned downstream from the sample-receiving member (1). The sample flows from position 1 in the direction of position 3. Opening of the locking member causes liquid to flow in the direction opposite to the sample flow, creating a reflux. The liquid subsequently flows towards reagents on a support, wherein said reagents at position 3 can react with analytes in the sample, generating a signal.
Figure 5:
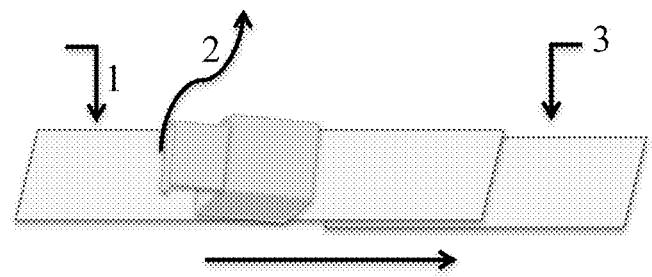
FIG. 5. Reflux device for detection of analytes in samples. One pulling or sliding locking member (2) is positioned downstream from the sample-receiving member (1). The sample flows from position 1 in the direction of position 3. Opening of the locking member causes liquid to flow in the direction opposite to the sample flow, creating a reflux. The liquid subsequently flows towards position 3, and immobilized reagents reacts with analytes in the sample, generating a signal.
Figure 6:
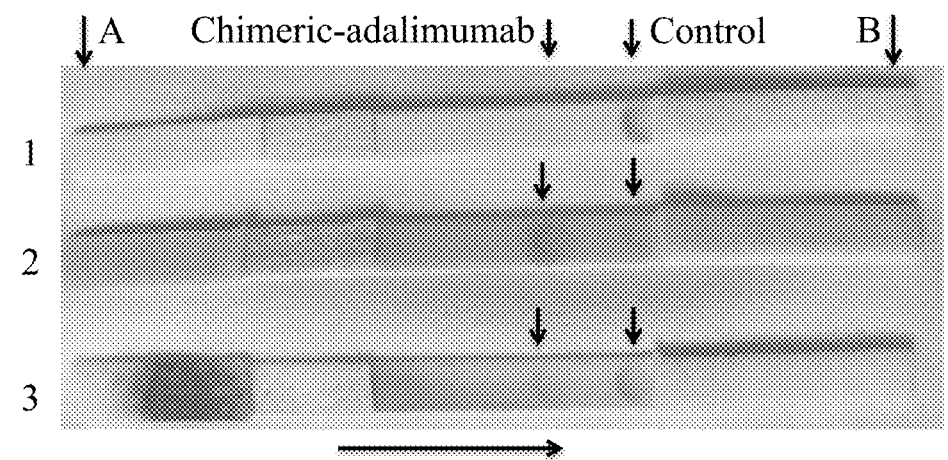
FIG. 6. Test strips for lateral flow immunoassay of anti-adalimumab antibodies.

FIG. 6 shows a non-limiting example of an interior of a device, which is included in embodiments of the present invention. Samples flow from A to B. Test strips for lateral flow assay are composed of (in this order): a sample pad (CytoSep 1660; Ahlstrom); a pad (ReliaFlow, Ahlstrom) containing latex-labeled goat anti-human IgG; a membrane (Hi-Flow HF075, Millipore) where both a control antibody (rabbit anti-goat IgG, Thermo Fisher) and a chimeric antibody ("chimeric-adalimumab") were immobilized, the latter being composed of the adalimumab variable region fused with mouse IgG2a constant region (Anti-hTNF-α-mIgG2a, InvivoGen); an absorbent pad (cellulose fiber, Millipore). 1, no anti-adalimumab antibody in the buffer sample; 2, anti-adalimumab antibody (HCA204, AbD Serotec) spiked on the buffer sample; 3, anti-adalimumab antibody (HCA204) spiked on 8 µl of blood. Following sample application, 80 µl of buffer (10 mM phosphate buffer pH 7.4, plus 137 mM NaCl, plus 0.02% triton-X-100) was added to the edge of the sample pad (position "A"), upstream from the sample. Although the sample pad is composed of a bibulous material designed to retain blood cells, the flow can cause red blood cells to move into the membrane when liquid is applied above or upstream the sample. The leakage is more accentuated as the blood volume increases, and when the liquid is applied above the sample or upstream from the sample flow.

Example 2

FIG. 7 shows a non-limiting example of an interior of a reflux device, which is included in embodiments of the present invention. Samples flow from A to B. Test strips for lateral flow assay are composed of (in this order): a sample pad (VF2; Whatman); a second pad (ReliaFlow, Ahlstrom); a membrane (UniSart CN 95, Sartorius); an absorbent pad (Cellulose fiber, Millipore). 1, 100 μl 0.9% NaCl dispensed upstream from the blood sample, at position A; 2, 100 μl of buffer (10 mM phosphate buffer pH 7.4, plus 137 mM NaCl, plus 0.02% triton-X-100) was dispensed immediately downstream from the blood sample in an angle and contrary to the direction of sample flow; 3, 100 μl of 0.9% NaCl was dispensed immediately downstream from the blood sample in an angle, and contrary to the direction of sample flow. Although the sample pad is composed of a bibulous material design to retain blood cells, the flow in (1) causes red blood cells to move into the membrane when liquid is applied above or upstream the sample. Dispensing of the liquid in (2) and (3) created a reflux compelling cells to the edge (position A) prior to resuming liquid flow towards the membrane. The leakage is more accentuated as the blood volume increases.

Example 3

FIG. 8 shows a non-restrictive example of an interior of a reflux device, which is included in embodiments of the present invention. Samples flow from A to B. The test strips for lateral flow were composed of (in this order): a sample pad (CytoSep HV, Ahlstrom); a second pad (ReliaFlow, Ahlstrom); a membrane (HF075, Millipore); an absorbent pad (cellulose fiber, Millipore). Tests were performed with sheep blood obtained from Rockland Inc. (Limerick, Pa.); blood volumes of 5 μl, 10 μl, 15 μl, and 20 μl were dispensed at the end of the sample pad (position A), followed by 60 μl of buffer (10 mM phosphate buffer pH 7.4, plus 137 mM NaCl, plus 0.02% triton-X-100), said buffer dispensed in an angle and contrary to the direction of sample flow, to create a reflux. The corresponding drops of blood are shown to the right of the figure.

Example 4

FIG. 10 shows a non-limiting example of an interior of a device, which is included in embodiments of the present invention. Samples flow from A to B. Test strips for lateral flow assay are composed of (in this order): a sample pad (LF1, GE Healthcare); a second pad (ReliaFlow, Ahlstrom) containing latex-labeled goat anti-human IgG; a membrane (Hi-Flow HF075, Millipore) where both a control antibody (rabbit anti-goat IgG, Thermo Fisher) and a chimeric antibody (chimeric-adalimumab) were immobilized, the latter being composed of the adalimumab variable region fused with mouse IgG2a constant region (Anti-hTNF-α-mIg2a, InvivoGen); an absorbent pad (cellulose fiber, Millipore). 1, no anti-adalimumab antibody in the buffer sample (10 mM phosphate buffer pH 7.4, plus 137 mM NaCl, plus 0.02% triton-X-100); 2, 5 μl of sheep blood; 3, 1 μl of anti-adalimumab antibody (HCA204, 500 m/ml, AbD Serotec) spiked on 5 μl of sheep blood; 4, 1 μl of anti-adalimumab antibody (HCA204, 500 m/ml, AbD Serotec) spiked on 5 μl of sheep blood. Following sample application, 50 μl of buffer (10 mM phosphate buffer pH 7.4, plus 137 mM NaCl, plus 0.02% triton-X-100) was added downstream of the sample application in an angle, and contrary to the direction of sample flow, to create a reflux. Sheep blood was obtained from Rockland Inc. (Limerick, Pa.).

What is claimed is:
1. A device comprising:
 a. A sample-receiving port adjacent to a sample-collecting pad which is configured to allow a sample to be placed on the sample-collecting pad at a sample-collecting point;
 b. A detection zone which produces a signal in response to a sample analyte from the sample interacting with the detection zone, wherein the device is configured to cause the sample analyte to travel from the sample-collecting spot to the detection zone in a downstream direction;
 c. A first liquid reservoir placed in the downstream direction from the sample-receiving port and at a level above the sample-collecting pad, wherein said first liquid reservoir has a first liquid in a predetermined amount and the device is configured such that when the first liquid is released, the first liquid travels in an upstream direction, opposite to the downstream direction, to the sample-collecting point and then travels in the downstream direction after reaching the sample-collecting point; and
 d. A second liquid reservoir placed in the downstream direction from the first reservoir, wherein said second liquid reservoir has a second liquid and the device is configured such that when the second liquid is released, the second liquid travels in the downstream direction.
2. The device of claim 1, wherein the sample-receiving pad can retain one or more particulates selected from the group consisting of blood cells, microorganisms, tissue debris, solids in tumor homogenates, solids in tissue homogenates, particulate matter in testing samples.
3. The device of claim 1, further comprising a filter positioned in the downstream direction from the sample-receiving pad.
4. The device of claim 1, further comprising a connecting pad that allows the sample to flow towards one or more reagents immobilized on the detection zone, and wherein binding of the sample analyte with the one or more reagents results in the signal.
5. The device of claim 4, wherein the device is configured to quantify the signal generated upon binding of the sample analyte to the one or more immobilized reagents.
6. The device of claim 1, further comprising an attached lancet.
7. A system comprising the device of claim 1, and further comprising encapsulated blood drops or blood samples of measured volumes, wherein said measured volumes are provided on the device itself or on an accompanying tool or set or instructions.
8. A device comprising:
 a. A sample-receiving port adjacent to a sample-collecting pad which is configured to allow a sample to be placed on the sample-collecting pad at a sample-collecting point;
 b. A detection zone which produces a signal in response to a sample analyte from the sample interacting with the detection zone, wherein the device is configured to cause the sample analyte to travel from the sample-collecting spot to the detection zone in a downstream direction; and
 c. A liquid reservoir placed in the downstream direction from the sample-receiving port and at a level above the sample-collecting pad, wherein said liquid reservoir has a liquid in a predetermined amount and the device is configured such that when the liquid is released, the liquid travels in an upstream direction, opposite to the downstream direction, to the sample-collecting point and then travels in the downstream direction after reaching the sample-collecting point.

9. The device of claim 8, wherein the sample-receiving pad can retain one or more particulates selected from the group consisting of blood cells, microorganisms, tissue debris, solids in tumor homogenates, solids in tissue homogenates, particulate matter in testing samples.

10. The device of claim 8, further comprising a filter positioned in the downstream direction from the sample-receiving pad.

11. The device of claim 8, further comprising a connecting pad that allows the sample to flow towards one or more reagents immobilized on the detection zone, and wherein binding of the sample analyte with the one or more reagents results in the signal.

12. The device of claim 11, wherein the device is configured to quantify the signal generated upon binding of the sample analyte to the one or more immobilized reagents.

13. The device of claim 8, further comprising an attached lancet.

14. A system comprising the device of claim 8, and
further comprising encapsulated blood drops or blood samples of measured volumes, wherein said measured volumes are provided on the device itself or on an accompanying tool or set or instructions.

* * * * *